(12) United States Patent
Shilev et al.

(10) Patent No.: US 9,326,810 B2
(45) Date of Patent: *May 3, 2016

(54) MULTI-BUTTON ELECTROSURGICAL APPARATUS

(71) Applicant: Bovie Medical Corporation, Clearwater, FL (US)

(72) Inventors: Nickolay Dimitrov Shilev, Sofia (BG); Gregory A. Konesky, Hampton Bays, NY (US)

(73) Assignee: Bovie Medical Corporation, Clearwater, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/679,183

(22) Filed: Apr. 6, 2015

(65) Prior Publication Data

US 2015/0209098 A1    Jul. 30, 2015

Related U.S. Application Data

(63) Continuation of application No. 13/966,034, filed on Aug. 13, 2013, now Pat. No. 8,998,899, which is a continuation-in-part of application No. 13/802,572, filed on Mar. 13, 2013, now Pat. No. 9,144,453, which (Continued)

(51) Int. Cl.
*A61B 18/18* (2006.01)
*A61B 18/14* (2006.01)

(Continued)

(52) U.S. Cl.
CPC ............... *A61B 18/14* (2013.01); *A61B 18/04* (2013.01); *A61B 18/042* (2013.01);

(Continued)

(58) Field of Classification Search
CPC combination set(s) only.
See application file for complete search history.

(56) References Cited

U.S. PATENT DOCUMENTS

| 1,813,902 | A | 7/1931 | Bovie |
| 2,435,442 | A | 2/1948 | Gurewitsch |

(Continued)

FOREIGN PATENT DOCUMENTS

| EP | 0878263 | 11/1998 |
| EP | 1764057 | 3/2007 |

(Continued)

OTHER PUBLICATIONS

European Search Report for European Application No. 13005083.4; dated Sep. 23, 2014; six (6) pages.

*Primary Examiner* — Robert N Wieland
(74) *Attorney, Agent, or Firm* — Gerald E. Hespos; Michael J. Porco; Matthew T. Hespos

(57) ABSTRACT

A multi-button electrosurgical apparatus includes a housing having a passage extending therethough, a distal end configured to support an electrode; at least four switches disposed on a surface of the housing configured to be selectively activated by a user; and three wires connected between the housing and a connector, the connector configured to be operatively coupled to an electrosurgical generator, a first wire being coupled to the electrode and configured to receive electrosurgical energy from the electrosurgical generator, a second wire being coupled to a first switch and configured to generate a first activation signal and a third wire being coupled to a second switch and configured to generate a second activation signal, wherein a third and fourth switch are coupled to the first wire and the second or third wire via a respective reactive switching element configured to generate third and fourth activation signals.

23 Claims, 12 Drawing Sheets

Related U.S. Application Data is a continuation-in-part of application No. 13/289,060, filed on Nov. 4, 2011, now Pat. No. 9,060,765.

(60) Provisional application No. 61/411,174, filed on Nov. 8, 2010.

(51) Int. Cl.
*A61B 18/04* (2006.01)
*A61B 17/3209* (2006.01)
*A61B 18/00* (2006.01)
*A61B 18/12* (2006.01)
*A61B 19/00* (2006.01)

(52) U.S. Cl.
CPC ........ *A61B 18/1206* (2013.01); *A61B 18/1402* (2013.01); *A61B 17/3209* (2013.01); *A61B 2018/00178* (2013.01); *A61B 2018/00589* (2013.01); *A61B 2018/00607* (2013.01); *A61B 2018/00922* (2013.01); *A61B 2018/00928* (2013.01); *A61B 2018/00988* (2013.01); *A61B 2018/128* (2013.01); *A61B 2018/1286* (2013.01); *A61B 2018/1412* (2013.01); *A61B 2018/1475* (2013.01); *A61B 2019/4857* (2013.01)

(56) References Cited

U.S. PATENT DOCUMENTS

| | | |
|---|---|---|
| 3,239,730 A | 3/1966 | Farago |
| 3,801,766 A | 4/1974 | Morrison |
| 4,127,110 A | 11/1978 | Bullara |
| 4,545,375 A | 10/1985 | Cline |
| 4,580,562 A | 4/1986 | Goof et al. |
| 4,619,258 A | 10/1986 | Pool |
| 4,625,723 A | 12/1986 | Altnether |
| 4,632,109 A | 12/1986 | Paterson |
| 4,708,137 A | 11/1987 | Tsukagoshi |
| 4,827,927 A | 5/1989 | Newton |
| 5,088,997 A | 2/1992 | Delahuerga et al. |
| 5,098,430 A | 3/1992 | Fleenor |
| 5,207,675 A | 5/1993 | Canady |
| 5,256,138 A | 10/1993 | Burek et al. |
| 5,269,780 A | 12/1993 | Roos |
| 5,306,238 A | 4/1994 | Fleenor |
| 5,400,267 A | 3/1995 | Denen et al. |
| 5,425,375 A | 6/1995 | Chin et al. |
| 5,449,356 A | 9/1995 | Walbrink et al. |
| 5,626,575 A | 5/1997 | Crenner |
| 5,651,780 A | 7/1997 | Jackson et al. |
| 5,660,657 A | 8/1997 | Rajala et al. |
| 5,693,042 A | 12/1997 | Boiarski et al. |
| 5,693,044 A | 12/1997 | Cosmescu |
| 5,776,092 A | 7/1998 | Farin et al. |
| 5,800,427 A | 9/1998 | Zamba |
| 6,193,715 B1 | 2/2001 | Wrublewski et al. |
| 6,293,945 B1 | 9/2001 | Parins et al. |
| 6,325,799 B1 | 12/2001 | Goble |
| 6,391,027 B1 | 5/2002 | Farin et al. |
| 6,409,724 B1 | 6/2002 | Penny et al. |
| 6,458,125 B1 | 10/2002 | Cosmescu |
| 6,558,383 B2 | 5/2003 | Cunningham et al. |
| 6,578,579 B2 | 6/2003 | Burnside et al. |
| 6,652,514 B2 | 11/2003 | Ellman |
| 6,770,071 B2 | 8/2004 | Woloszko et al. |
| 6,899,538 B2 | 5/2005 | Matoba |
| 6,958,063 B1 | 10/2005 | Soll et al. |
| 6,994,707 B2 | 2/2006 | Ellman |
| 7,115,121 B2 | 10/2006 | Novak |
| 7,156,842 B2 | 1/2007 | Sartor |
| 7,156,844 B2 | 1/2007 | Reschke |
| 7,244,257 B2 | 7/2007 | Podhajsky |
| 7,316,682 B2 | 1/2008 | Konesky |
| 7,335,199 B2 | 2/2008 | Goble et al. |
| 7,443,296 B2 | 10/2008 | Mezhinsky et al. |
| 7,479,140 B2 | 1/2009 | Ellman et al. |
| 7,481,809 B2 | 1/2009 | Stern et al. |
| 7,503,917 B2 | 3/2009 | Sartor |
| 7,568,619 B2 | 8/2009 | Todd et al. |
| 7,578,817 B2 | 8/2009 | Canady |
| 7,654,975 B2 | 2/2010 | Mantell |
| 7,815,638 B2 | 10/2010 | Farin et al. |
| 8,016,824 B2 | 9/2011 | Buchman |
| 8,022,327 B2 | 9/2011 | Blomeyer |
| 8,177,782 B2 | 5/2012 | Beller et al. |
| 8,216,220 B2 | 7/2012 | Jensen |
| 8,319,134 B2 | 11/2012 | Blomeyer |
| 8,353,905 B2 | 1/2013 | Jensen |
| 8,562,598 B2 | 10/2013 | Falkenstein et al. |
| 8,568,400 B2 | 10/2013 | Gilbert |
| 2002/0013582 A1 | 1/2002 | Mulier et al. |
| 2003/0050633 A1 | 3/2003 | Ellman et al. |
| 2003/0130655 A1 | 7/2003 | Woloszko et al. |
| 2004/0148903 A1 | 8/2004 | Cash |
| 2004/0243120 A1 | 12/2004 | Orszulak et al. |
| 2005/0075630 A1 | 4/2005 | Truckai et al. |
| 2005/0148903 A1 | 7/2005 | Diamantopoulos |
| 2006/0122595 A1 | 6/2006 | Farin et al. |
| 2007/0028669 A1 | 2/2007 | Brewster |
| 2007/0049926 A1 | 3/2007 | Sartor |
| 2007/0083247 A1 | 4/2007 | Wyeth et al. |
| 2007/0093810 A1 | 4/2007 | Sartor |
| 2007/0135812 A1 | 6/2007 | Sartor |
| 2007/0260239 A1 | 11/2007 | Podhajsky |
| 2008/0071261 A1 | 3/2008 | Orszulak |
| 2008/0108985 A1 | 5/2008 | Konesky |
| 2008/0140066 A1 | 6/2008 | Davison et al. |
| 2009/0143778 A1 | 6/2009 | Sartor |
| 2009/0149851 A1 | 6/2009 | Craig |
| 2009/0248022 A1 | 10/2009 | Falkenstein et al. |
| 2010/0262139 A1 | 10/2010 | Beller et al. |
| 2011/0276113 A1 | 11/2011 | Cybulski |
| 2012/0116397 A1 | 5/2012 | Rencher et al. |
| 2012/0123405 A1* | 5/2012 | Moua ............... A61B 18/12 606/33 |
| 2012/0232540 A1 | 9/2012 | Baur et al. |
| 2012/0330305 A1 | 12/2012 | Zoran et al. |
| 2012/0330307 A1 | 12/2012 | Ladtkow |
| 2013/0046290 A1 | 2/2013 | Palmer |
| 2013/0237982 A1 | 9/2013 | Rencher et al. |
| 2013/0296846 A1 | 11/2013 | Canady et al. |
| 2014/0005665 A1 | 1/2014 | Konesky et al. |
| 2014/0018795 A1 | 1/2014 | Shilev et al. |

FOREIGN PATENT DOCUMENTS

| | | |
|---|---|---|
| EP | 2263728 | 12/2010 |
| EP | 2449992 | 5/2012 |
| WO | 2004096315 | 11/2004 |

* cited by examiner

VOLTAGE SOURCE WITH AMPLITUDE DETECTOR

CURRENT SOURCE WITH AMPLITUDE DETECTOR

VOLTAGE/CURRENT SOURCE WITH DUTY CYCLE MEASUREMENT

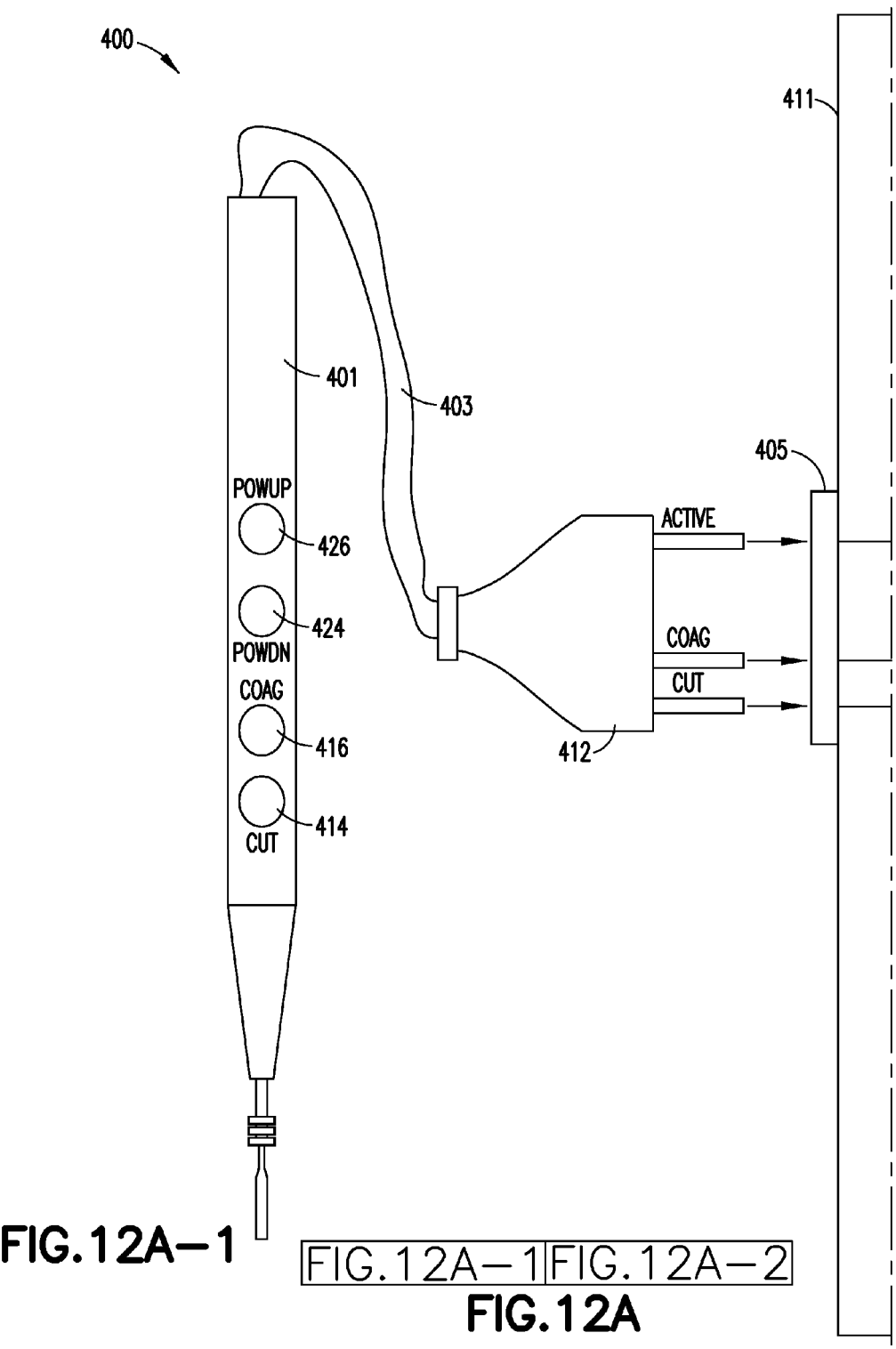

MULTI-BUTTON ELECTROSURGICAL APPARATUS

PRIORITY

This application is a continuation application of U.S. application Ser. No. 13/966,034 filed Aug. 13, 2013, now U.S. Pat. No. 8,998,899, which is a continuation-in-part application of U.S. application Ser. No. 13/802,572 filed Mar. 13, 2013, now U.S. Pat. No. 9,144,453, which is a continuation-in-part application of U.S. application Ser. No. 13/289,060 filed Nov. 4, 2011, now U.S. Pat. No. 9,060,765, which claims priority on U.S. Provisional Patent Appl. No. 61/411,174, filed Nov. 8, 2010, the content of all of which are hereby incorporated by reference in their entireties.

BACKGROUND

1. Field

The present disclosure relates generally to electrosurgery and electrosurgical systems and apparatuses, and more particularly, to an electrosurgical apparatus with a multi-button handpiece.

2. Description of the Related Art

High frequency electrical energy has been widely used in surgery. Tissue is cut and bodily fluids are coagulated using electrosurgical energy generated by an electrosurgical unit (ESU), e.g., an electrosurgical generator, and delivered or applied to the tissue by an electrosurgical instrument, e.g., a handpiece.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. In the latter example, the process can be relatively slow, generate large volumes of noxious smoke with vaporized and charred tissue, and may cause collateral damage to surrounding healthy tissue when high power electrosurgical energy is used. Precision accuracy can also be a problem, due to the width of the plasma beam.

The power of any electrosurgical unit (ESU) or RF-unit (radio frequency unit) is delivered to the patient tissue by an activation command, given by the surgeon. The command interface is usually switches (e.g., buttons), located in the activation accessories of the ESU, e.g., handles (handpieces), footswitches and other special instruments. A conventional handle accessory 10 is illustrated in FIG. 1 and includes a housing 2, an electrode 8 and two buttons—one for CUT mode (button 14) and one for COAG mode (button 16). Typically, the buttons 14, 16 are colored by the requirements of specific standards, e.g., yellow for CUT mode, and blue for COAG mode. The 2-button handle 10 uses 3 wires to connect to the ESU 11 via connector 12 and cable 13.

During the course of an electrosurgical procedure, the power setting of each mode may need to be changed several times to adapt to varying operative conditions. Conventionally, this is done by making adjustments on the control panel of the electrosurgical generator unit, and would either need the assistance of a nurse, or require the surgeon to leave the sterile field of the surgical site. It would be advantageous for the surgeon to be able to adjust the electrosurgical power on an as-needed basis by adding additional controls to the electrosurgical hand piece itself. However, additional buttons would require more control wires from the handpiece 10 to the ESU 11; for example, a handle with 3 buttons would require 4 control wires, a handle with 4 buttons would require 5 control wires, i.e., the number of required control wires=the number of buttons+1.

Consequentially, more control wires in the cable 13 between the handpiece 10 and the ESU 11 has at least two disadvantages. First, additional control wires increases the complexity, and hence costs, of the connectors for the handpiece and for the front panel of the ESU. Increased cost is a critical issue in the case of disposable accessories. Secondly, more wires in the cable usually represents more stray capacitance to earth, hence higher leakage currents will be produced. Higher leakage currents are to be avoided when working with higher frequencies, e.g., up to 4 MHz.

Therefore, a need exists for a multi-button handpiece or accessory for controlling an electrosurgical unit or generator that employs a minimum number of control wires.

SUMMARY

The present disclosure relates to an electrosurgical apparatus with a multi-button handpiece.

According to one aspect of the present disclosure, an electrosurgical apparatus is provided including a housing having a passage extending therethough, the housing having a proximal end and a distal end, the distal end configured to support an electrode; at least four switches disposed on a surface of the housing configured to be selectively activated by a user; and three wires connected between the housing and a connector, the connector configured to be operatively coupled to an electrosurgical generator, a first wire being coupled to the electrode and configured to receive electrosurgical energy from the electrosurgical generator, a second wire being coupled to a first switch and configured to generate a first activation signal and a third wire being coupled to a second switch and configured to generate a second activation signal, wherein a third and fourth switch are coupled to the first wire and the second or third wire via a respective reactive switching element configured to generate third and forth activation signals.

In one aspect, the at least four switches are configured as pushbuttons.

In another aspect, each of the respective reactive switching elements is selected to generate a different impedance value.

In yet another aspect, each of the respective reactive switching elements may include a parallel combination of a resistor and a capacitor, a series combination of a resistor and an inductor, a series combination of a resistor and a capacitor, a parallel combination of a resistor and an inductor, a capacitor or an inductor.

In a further aspect, the connector includes a three pin connector.

In another aspect, at least two switches of the at least four switches are coupled to a single rocker button.

In another aspect of the present disclosure, electrosurgical apparatus includes an electrosurgical generator coupled to an electrical power supply configured to generate electrosurgical energy; a handpiece including a housing having a passage extending therethough, the housing having a proximal end and a distal end, the distal end configured to support an electrode; at least four switches disposed on a surface of the housing configured to be selectively activated by a user; and three wires connected between the housing and a connector, the connector configured to be operatively coupled to the electrosurgical generator, a first wire being coupled to the electrode and configured to receive electrosurgical energy from the electrosurgical generator, a second wire being coupled to a first switch and configured to generate a first activation signal and a third wire being coupled to a second switch and configured to generate a second activation signal, wherein a third and fourth switch are coupled to the first wire and the second or third wire via a respective reactive switching element configured to generate third and forth activation signals; and an activation sense circuit configured to distinguish between the first, second, third and fourth activation signals and to execute a corresponding action.

In one aspect, the at least one activation sense circuit includes an oscillator generator and at least one transistor configured to operate as a voltage or current source for the reactive switching elements.

In another aspect, a frequency of the oscillator generator is different than an operating frequency of the electrosurgical generator.

In a further aspect, each of the respective reactive switching elements is selected to generate a different impedance value.

In yet another aspect, each of the first and second activation signals is a short circuit signal.

In one aspect, the at least one activation sense circuit includes a comparator to compare each of the third and fourth activation signals to a predetermined value.

In another aspect, the at least one activation sense circuit converts the third and fourth activation signals into a respective pulse width modulation (PWM) signal.

According to another aspect of the present disclosure, an electrosurgical apparatus inclues an electrosurgical generator coupled to an electrical power supply configured to generate electrosurgical energy; a handpiece including: a housing having a passage extending therethough, the housing having a proximal end and a distal end, the distal end configured to support an electrode; at least four switches disposed on a surface of the housing configured to be selectively activated by a user; and three wires connected between the housing and a connector, the connector configured to be operatively coupled to the electrosurgical generator, a first wire being coupled to the electrode and configured to receive electrosurgical energy from the electrosurgical generator, a second wire being coupled to a first switch and configured to generate a first activation signal and a third wire being coupled to a second switch and configured to generate a second activation signal, wherein a third and fourth switch are coupled to the first wire and the second or third wire via a respective resonant circuit configured to generate third and forth activation signals; and at least one activation sense circuit configured to distinguish between the first, second, third and fourth activation signals and to execute a corresponding action.

In one aspect, each respective resonant circuit is configured for a different frequency.

In a further aspect, the oscillator generator is a variable frequency oscillator generator configured to sweep through a predetermined range of frequencies, wherein the predetermined range of frequencies include the frequencies of the respective resonant circuits.

BRIEF DESCRIPTION OF THE DRAWINGS

The above and other aspects, features, and advantages of the present disclosure will become more apparent in light of the following detailed description when taken in conjunction with the accompanying drawings in which.

Figure 1:
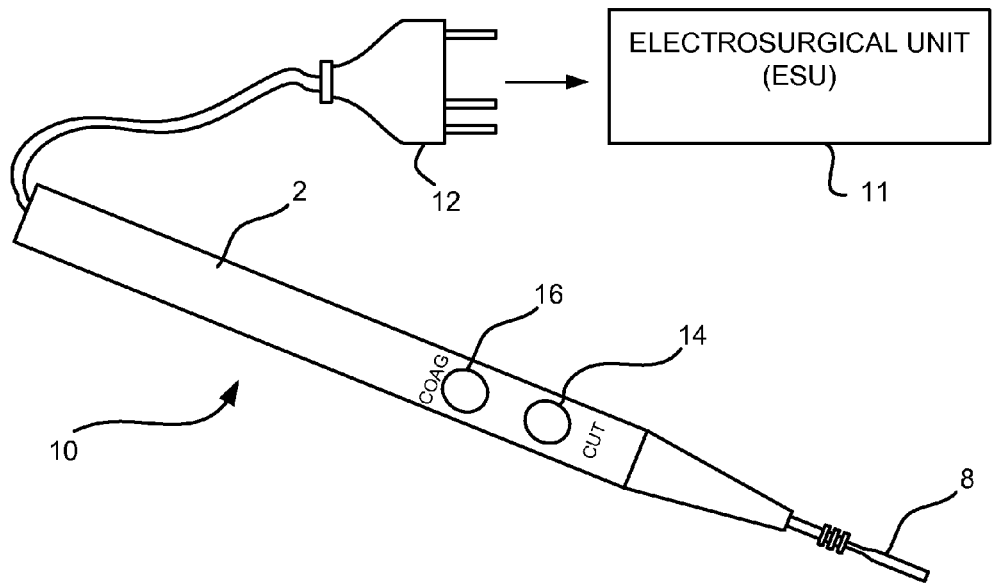
FIG. 1 is an illustration of an exemplary electrosurgical system in accordance with an embodiment of the present disclosure.

It should be understood that the drawing(s) is for purposes of illustrating the concepts of the disclosure and is not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

An electrosurgical apparatus with a multi-button handpiece is provided. The electrosurgical apparatus of the present disclosure provides a significant advantage for a surgeon to be able to adjust electrosurgical power on an as-needed basis by adding additional controls to an electrosurgical handpiece itself. The additional controls can take the form of two new pushbuttons, or a two-position switch, one for power-up and another for power-down, in addition to, for example, cut and coagulation pushbuttons already present on an electrosurgical handpiece, e.g., an electrosurgical pencil. The techniques of the present disclosure provide a way that no additional signal lines, and associated connector pins would be needed as these would add to the overall cost of the hand piece assembly, where cost is a particularly sensitive aspect of disposable medical devices. By keeping the signal lines to a minimum, e.g., three signal lines, stray capacitance and therefore higher leakage currents can be avoided, which is especially problematic in electrosurgical generators that operate at higher frequencies, such as 4 MHz.

Figure 2:
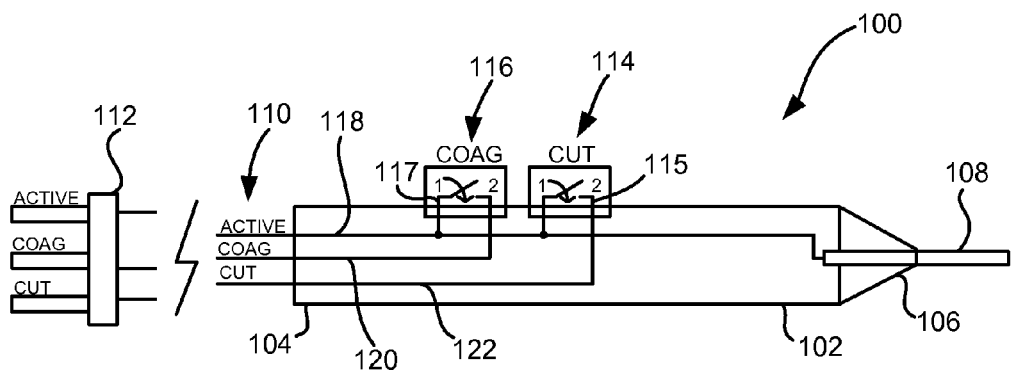
FIG. 2 is an electrical schematic diagram of an electrosurgical handpiece in accordance with an embodiment of the present disclosure.

Referring to FIG. 2, an electrical schematic diagram of an electrosurgical handpiece in accordance with an embodiment of the present disclosure is provided. The handpiece 100 includes a housing 102 having a passage extending therethough, the housing 102 having a proximal end 104 and a distal end 106. The distal end 106 of the housing is configured to support a conductive element 108, e.g., a blade electrode, for affecting a surgical procedure to tissue. A cable 110 couples the proximal end 104 of the handpiece 100 to a connector 112. The connector 112 is configured to be coupled to a corresponding connector on a face of the ESU. First and second buttons 114, 116, i.e., a CUT button and a COAG button respectively, are disposed on an outer surface of the housing 102 to initiate different electrosurgical procedures. The first and second buttons 114, 116 are coupled to respectively switches 115, 117.

The cable 110 carries three conductors or wires from the connector 112 to the handpiece 100. A first conductor 118, labeled ACTIVE in FIG. 2, couples an RF or electrosurgical power output from the ESU to the blade electrode 108. One pole of each switch 115, 117 is also coupled to the first conductor 118. A second conductor 120, labeled COAG in FIG. 2, is coupled to a second pole of the switch 117 controlled by button 116. A third conductor 122, labeled CUT in FIG. 2, is coupled to a second pole of the switch 115 controlled by button 114. The cut and coagulation pushbuttons operate by making contact with the active electrode, which carries the operative electrosurgical power. This implementation then requires only three wires and an associated three pin connector 112, as illustrated in FIG. 2, between the handpiece 100 and ESU.

Figure 3:
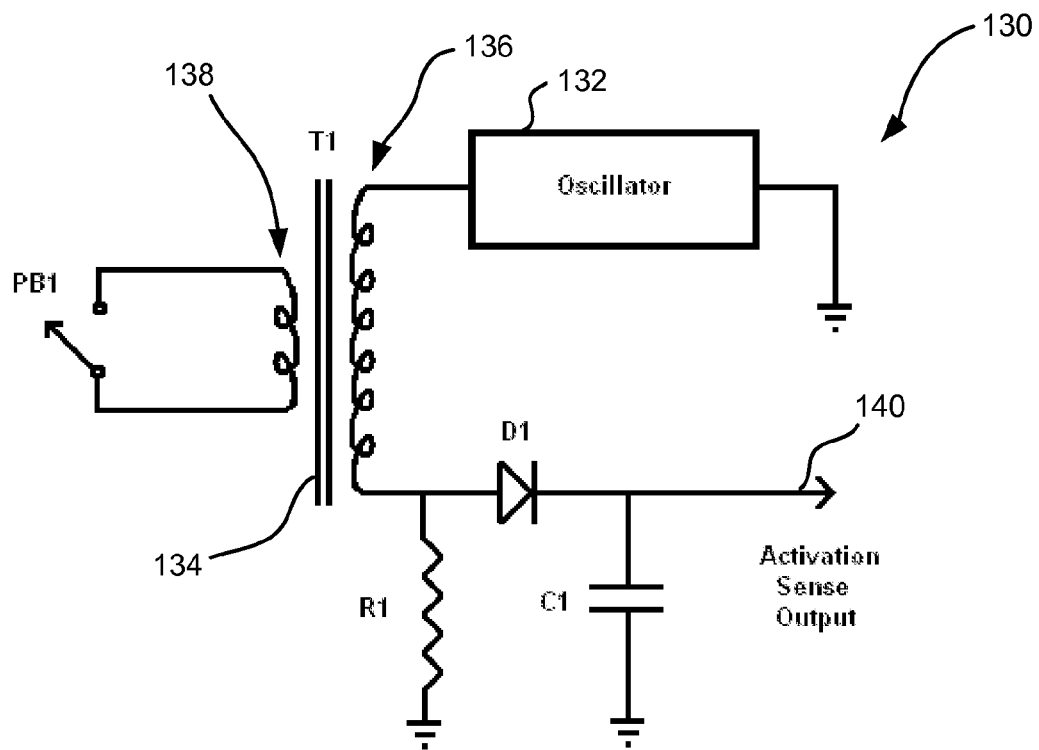
FIG. 3 is a pushbutton activation sensing circuit in accordance with an embodiment of the present disclosure.
Figure 4:
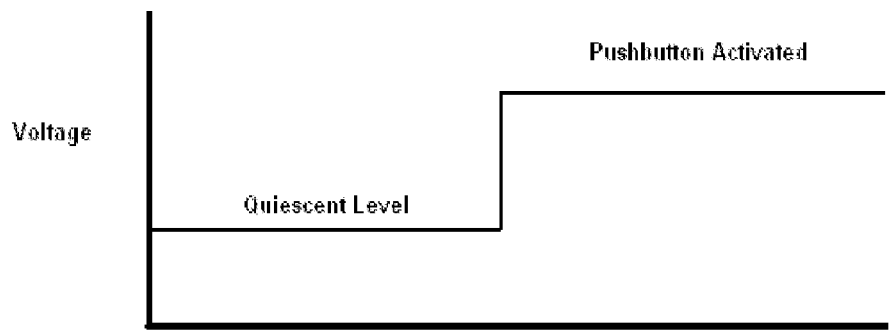
FIG. 4 is an illustration of an activation sense output in accordance with an embodiment of the present disclosure.

A means of isolation is necessary from the signal generated when either the cut or coagulation pushbuttons are activated and are connected to the active power line 118 since the active power level carries very high voltages, incompatible with digital control logic levels. The means of isolation can be achieved with an isolation barrier transformer and associated activation circuit, for example, disposed in the electrosurgical generator. Pushbutton actuation is sensed using an activation sense circuit 130, which is illustrated in FIG. 3. The activation sense circuit 130 includes an oscillator 132 which drives the secondary 136 of an isolation transformer T1 134. The frequency of the oscillator 132 is chosen so that it is significantly different than operating frequency of the electrosurgical generator, to prevent one from being mistaken from the other. A pushbutton PB1 (e.g., button 114 or button 116) is connected across the primary 138 of the isolation transformer T1 134, by way of the active line and either the cut or coagulation lines. The alternating current flowing in the secondary 136 of the isolation transformer T1 134 is monitored by resistor R1 and is at a given quiescent level when the pushbutton PB1 is not activated, and the primary 138 of the isolation transformer 134 is open-circuit. This quiescent current is rectified and filtered by diode D1 and filter capacitor C1, producing a quiescent DC level. However, when the pushbutton PB1 is activated, the pushbutton or switch short-circuits the primary 138 of the isolation transformer T1 134, causing a substantial increase in the current of the secondary 136 of the isolation transformer 134 that results in an increase in the DC level at the activation sense output 140, which is illustrated in FIG. 4. It is this increase in secondary current that is sensed and recognized as a valid pushbutton activation via a controller or other circuitry in the ESU. A complete set of an isolation transformer and activation circuit is needed for each pushbutton.

When the activation of a pushbutton is sensed, in addition to commanding the associated function in the electrosurgical generator, such as cut or coagulation, a feedback signal may also be produced to alert the user of the activation. Both visual feedback, in the form of an indicator light on the electrosurgical generator front panel, and an auditory tone are produced, and each are unique and easily distinguished for either cut or coagulation activation.

Figure 9:
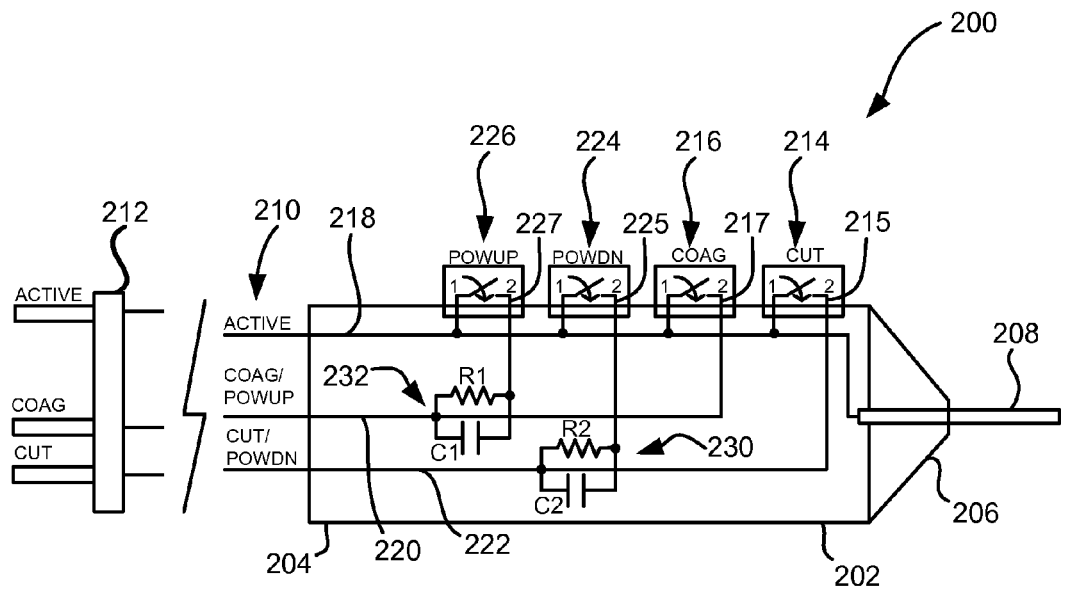
FIG. 9 is an electrical schematic diagram of an electrosurgical handpiece in accordance with another embodiment of the present disclosure.
Figure 9A:
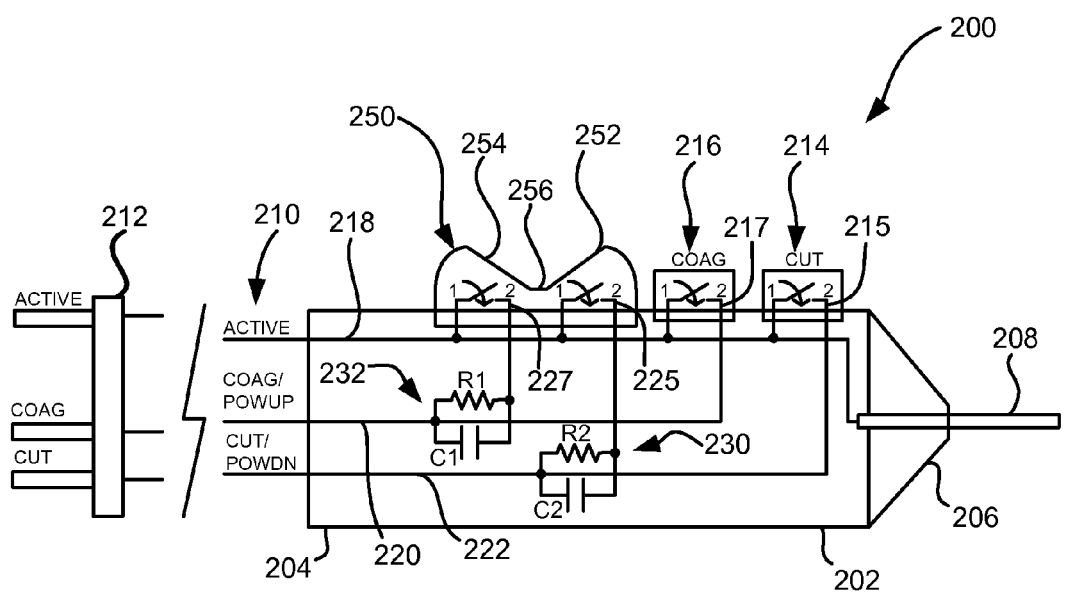
FIG. 9A is an electrical schematic diagram of an electrosurgical handpiece in accordance with a further embodiment of the present disclosure.
Figures 2, 12A:
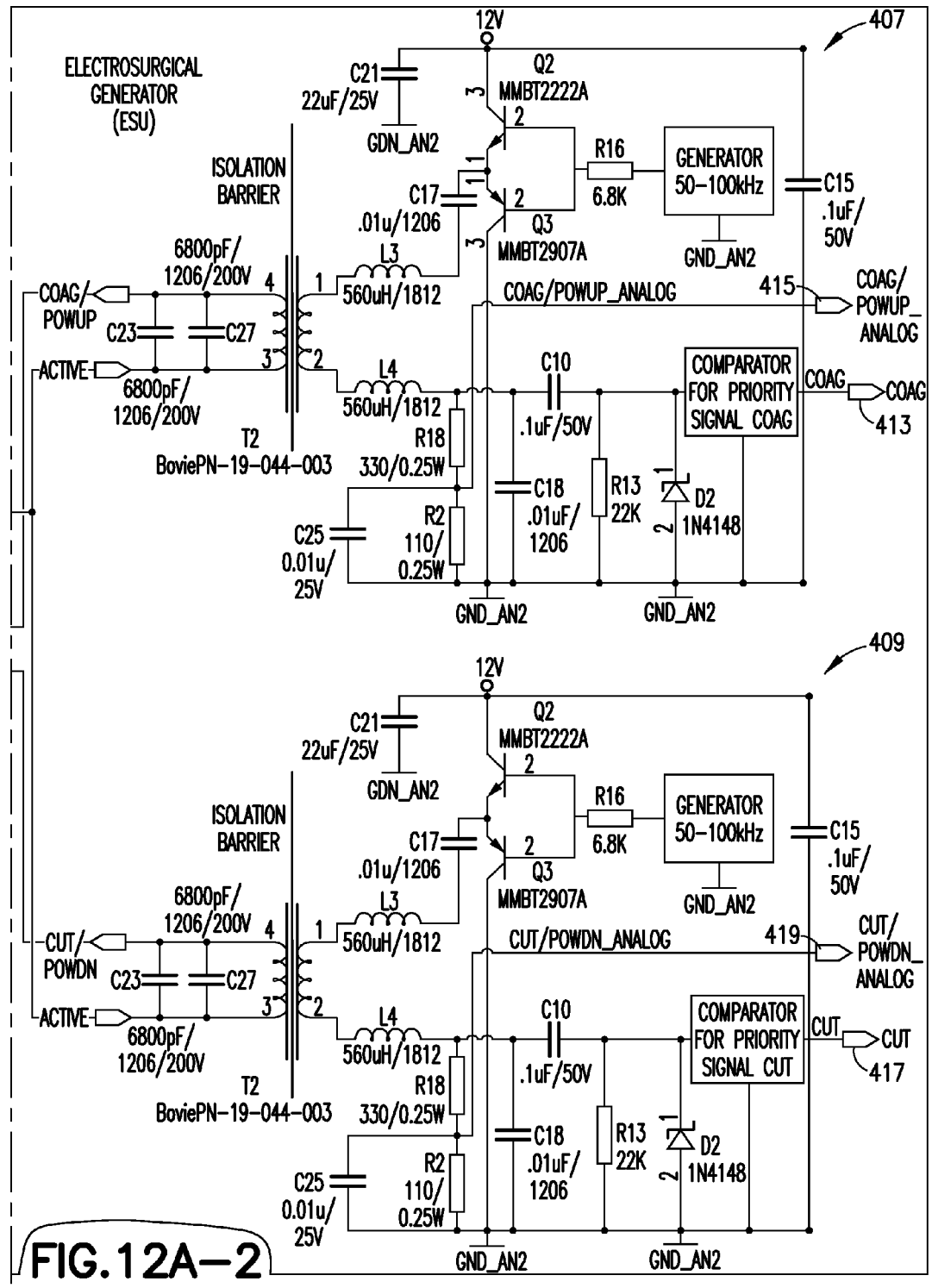
FIGS. 12A-12C illustrate an electrosurgical system in accordance with an embodiment of the present disclosure.

Additional pushbuttons can be added in parallel with the cut and coagulation pushbuttons, but instead switch in a specific impedance value, other than the short circuit value if the cut or coagulation pushbuttons were activated. An exemplary handpiece including two additional pushbuttons for power-up and power-down functions is illustrated in FIGS. 9, 9A and 12A, the details of which will be described below.

Figure 5A:
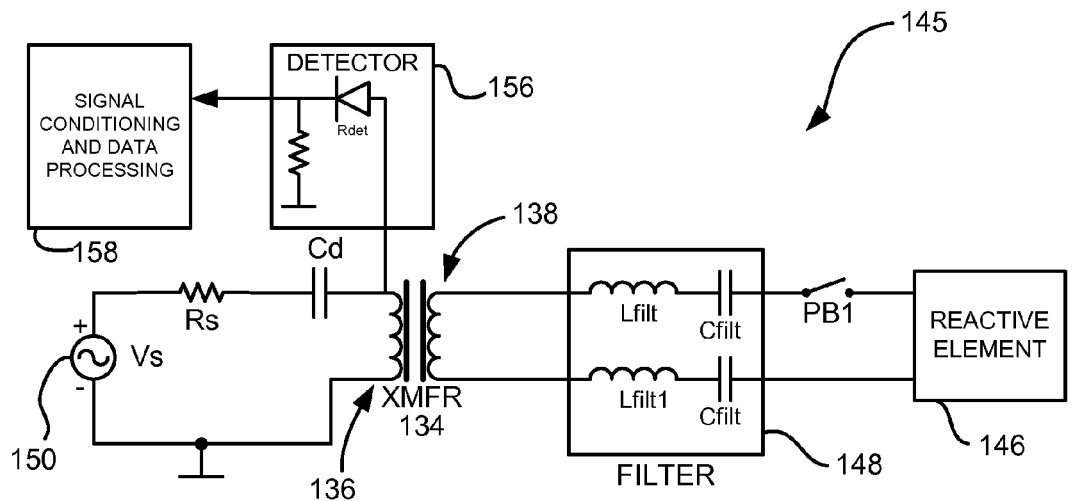
FIG. 5A is an illustration of an activation sensing circuit employing a voltage source with an amplitude detector in accordance with an embodiment of the present disclosure.
Figure 5B:
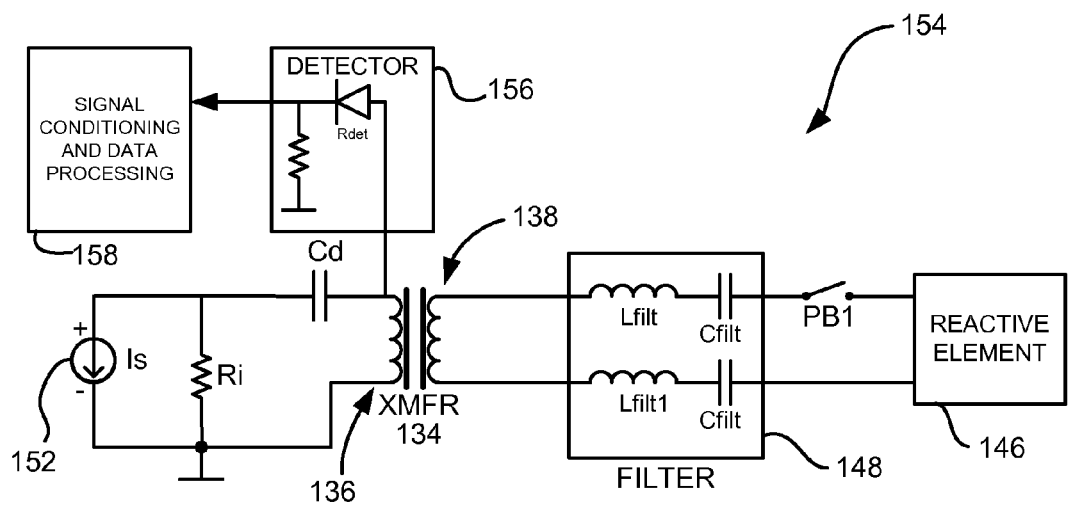
FIG. 5B is an illustration of an activation sensing circuit employing a current source with an amplitude detector in accordance with an embodiment of the present disclosure.

Referring to the activation sense circuit 130 in FIG. 3, instead of introducing a short circuit of pushbutton PB1 introduced into the primary 138 of transformer T1 134, an activation sense circuit 145 may include a reactive element 146 that can be switched-in as shown in FIG. 5A. This will cause an increase in the secondary current of transformer T1 134 which is somewhat less than the short circuit value, as shown in FIG. 4. This increased secondary current value will depend on the impedance value of the reactive element 146 at a given frequency. The activation sense circuit 145 of FIG. 5A may also include an optional filter circuit 148 on the primary side 138 of the transformer 134 which is used to both prevent the electrosurgical power signal and any noise generated by the electrosurgical discharge arc, from interfering with the recognition of an activation signal. The oscillator 150 in FIG. 5A is configured as a voltage source, while the oscillator may be configured as a current source 152 as shown in activation sense circuit 154 in FIG. 5B. Capacitor Cd in FIGS. 5A and 5B is used to block any DC component which may be present in the oscillator output. The output from detector 156 in either FIGS. 5A and 5B is further filtered and sent to an analog to digital converter (ADC) (not shown) whose value is then used to determine if the pushbutton PB1 is pressed by the electrosurgical generator system controller 158 by comparing it to a preset fixed value. Alternately, the filtered output of the detector 156 can be sent to a comparator which compares it to a fixed reference voltage, and then determine if the pushbutton PB1 is pressed.

Figure 6:
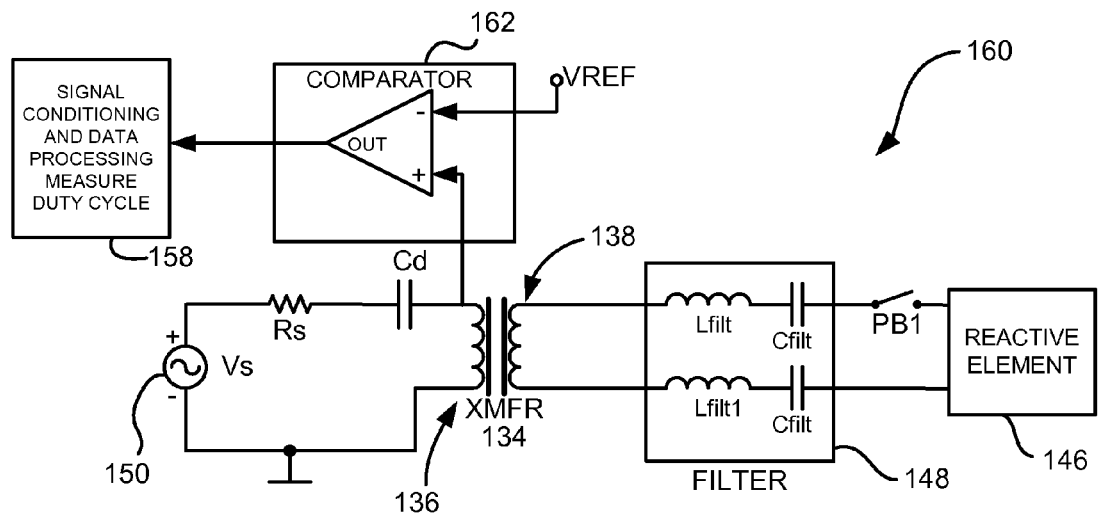
FIG. 6 is an illustration of an activation sensing circuit employing duty cycle measurement in accordance with an embodiment of the present disclosure.
Figure 7A:
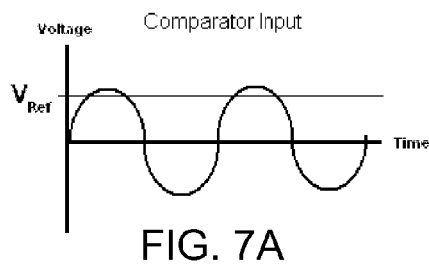
FIGS. 7A-7B illustrate input/output signals of the activation sensing circuit shown in FIG. 6 in accordance with one embodiment of the present disclosure.
Figure 8A:
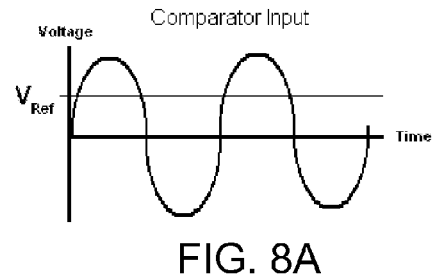
FIGS. 8A-8B illustrate input/output signals of the activation sensing circuit shown in FIG. 6 in accordance with another embodiment of the present disclosure.
Figure 7B:
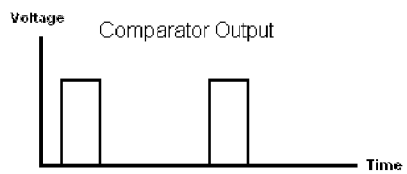
Figure 8B:
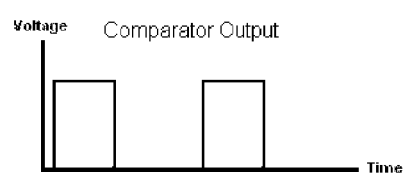

In an alternate configuration as shown in FIG. 6, activation sense circuit 160 converts the amplitude sensed at the secondary 136 of the transformer 134 into a pulse width modulation (PWM) signal with post measurement of the duty cycle. The activation sense circuit 160 utilizes a comparator 162 to sense the change in current in the secondary 136 of the transformer 134. The amplitude of the voltage sensed in the secondary 136 of the transformer 134 is compared to a reference voltage ($V_{REF}$). When the instantaneous sensed voltage exceeds the reference voltage ($V_{REF}$), the output of the comparator 162 goes to a logic "1" and is at a logic "0" otherwise. The higher the peak amplitude of the sensed voltage, the longer it will be above the reference voltage, and the longer the output of the comparator 162 will remain at a logic "1". This results in a pulse whose width is related to the amplitude of the sensed voltage. The higher the sensed peak voltage is, the wider the pulse. This is illustrated in FIG. 7A and the resulting comparator output in FIG. 7B for a lower sensed peak voltage, and for a higher sensed peak voltage in FIGS. 8A and 8B, respectively. This varying pulse width output from the comparator 162 is then measured by the controller 158 of the electrosurgical generator system and compared to preset values to determine if the pushbutton PB1 was pressed or is open. This substantially reduces the cost and complexity of an ADC-based configuration.

It is to be appreciated that the oscillator source, e.g., a voltage or current source, may be a self-oscillating circuit, for example, a Colpitz oscillator.

Referring to FIG. 9, an electrical schematic diagram of an electrosurgical handpiece 200 in accordance with another embodiment of the present disclosure is provided. The handpiece 200 includes a housing 202 having a passage extending therethough, the housing 202 having a proximal end 204 and a distal end 206. The distal end 206 of the housing is configured to support a conductive element 208, e.g., a blade electrode, for affecting a surgical procedure to tissue. A cable 210 couples the proximal end 204 of the handpiece 200 to a connector 212. The connector 212 is configured to be coupled to a corresponding connector on a face of the ESU. First and second buttons 214, 216, i.e., a CUT button and a COAG button respectively, are disposed on or through an outer surface of the housing 202 to initiate different electrosurgical procedures. The first and second buttons 214, 216 are coupled to respectively switches 215, 217. In this embodiment, third and fourth buttons 224, 226, i.e., a power down (POWDN) button and a power up (POWUP) button respectively, are also disposed on an outer surface of the housing 202. The third and fourth buttons 224, 226 are coupled to respectively switches 225, 227.

It is to be appreciated that although buttons 224, 226 are shown as two individual buttons, buttons 224, 226 may be replaced as a single rocker button which is coupled to switches 225, 227. Referring to FIG. 9A, rocker button or switch 250 is disposed on the outer surface of housing 202. The rocker button 250 includes first inclined surface 252 and second inclined surface 254 which are configured to pivot about central point 256, as is know in the art. The first inclined surface 252 is coupled to switch 225 (e.g., power down) and the second inclined surface is coupled to switch 227 (e.g., power up). Upon pressing either the first or second inclined surface by a user, the corresponding switch closes. The rocker button 250 may be spring-loaded so that it returns to a unactivated state, upon a release in pressure by the user, i.e., when neither the first nor second inclined surface is pressed, switch 225 and switch 227 are open. Other types of buttons and/or devices to activate switches 215, 217, 225, 227 are contemplated to be within the scope of the present disclosure. For example, the buttons and/or devices to activate the switches may include, but are not limited to, slider type switches, capacitance touch switches, resistance touch switches, etc.

Similar to the embodiment shown in FIG. 2, the cable 210 carries three conductors or wires from the connector 212 to the handpiece 200. A first conductor 218, labeled ACTIVE in FIG. 9, couples an RF or electrosurgical power output from the ESU to the blade electrode 208. One pole of each switch 215, 217 is also coupled to the first conductor 218. A second conductor 220, labeled COAG/POWUP in FIG. 9, is coupled to a second pole of the 217 switch controlled by button 216. A third conductor 222, labeled CUT/POWDN in FIG. 9, is coupled to a second pole of the 215 switch controlled by button 214.

It is to be appreciated that the third and fourth switches 225, 227 respectively are coupled to the three conductors 218, 220, 222 obviating the need for more control wires. As shown in FIG. 9, switch 225 has one pole coupled to conductor 218 and the second pole coupled to the conductor 222 via a reactive switching element 230, i.e., resistor R2 and capacitor C2. The switch 227 has one pole coupled to conductor 218 and the second pole coupled to the conductor 220 via reactive switching element 232, i.e., resistor R1 and capacitor C1.

The multi-button activation sensing circuit operates on a similar principle as described in relation to the circuit shown in FIG. 3, but now looks for a specific change in impedance, while still being compatible with the cut and coagulation pushbutton operation. Values for resistors and capacitors R1, C1 and R2, C2 shown in FIG. 9 are selected so that the change in impedance when the associated pushbutton is activated is easily distinguished from the short circuit when either the cut or coagulation pushbuttons are pressed. Exemplary values for resistors R1, R2 may be 100 ohms while capacitors C1, C2 may be 2.2 nF; however, these values are only exemplary values and other values of the resistors and capacitors are contemplated to be within the scope of the present disclosure. The cut and coagulation pushbuttons take priority, since once they are pressed, their short circuit makes it impossible to see either resistor and capacitor combination R1, C1 or R2, C2. As a result, the power level of the electrosurgical generator cannot be changed while a cut or coagulation activation is in progress, i.e., pressing the power up button 226 or power down button 224 will have no effect while the CUT button 214 or COAG button 216 is pressed.

Capacitors C1 and C2 shown in FIG. 9 are placed in parallel with resistors R1 and R2 respectively, both to reduce noise pickup, especially in the case of long cables between the electrosurgical hand piece and the electrosurgical generator, and to reduce the power dissipation in resistors R1 and R2. Without these capacitors, the power dissipation would be several Watts which would require physically large resistors in an electrosurgical hand piece where space is already limited. Since the impedance is being sensed through the parallel combination of resistor R1 and capacitor C1 and the parallel combination of resistor R2 and capacitor C2, it is to be appreciated that this change in impedance could also be affected by other reactive switching elements such as a series combination of a resistor and a capacitor, a series combination of a resistor and an inductor, a parallel combination of a resistor and an inductor, or a capacitor or an inductor alone.

Figure 10:
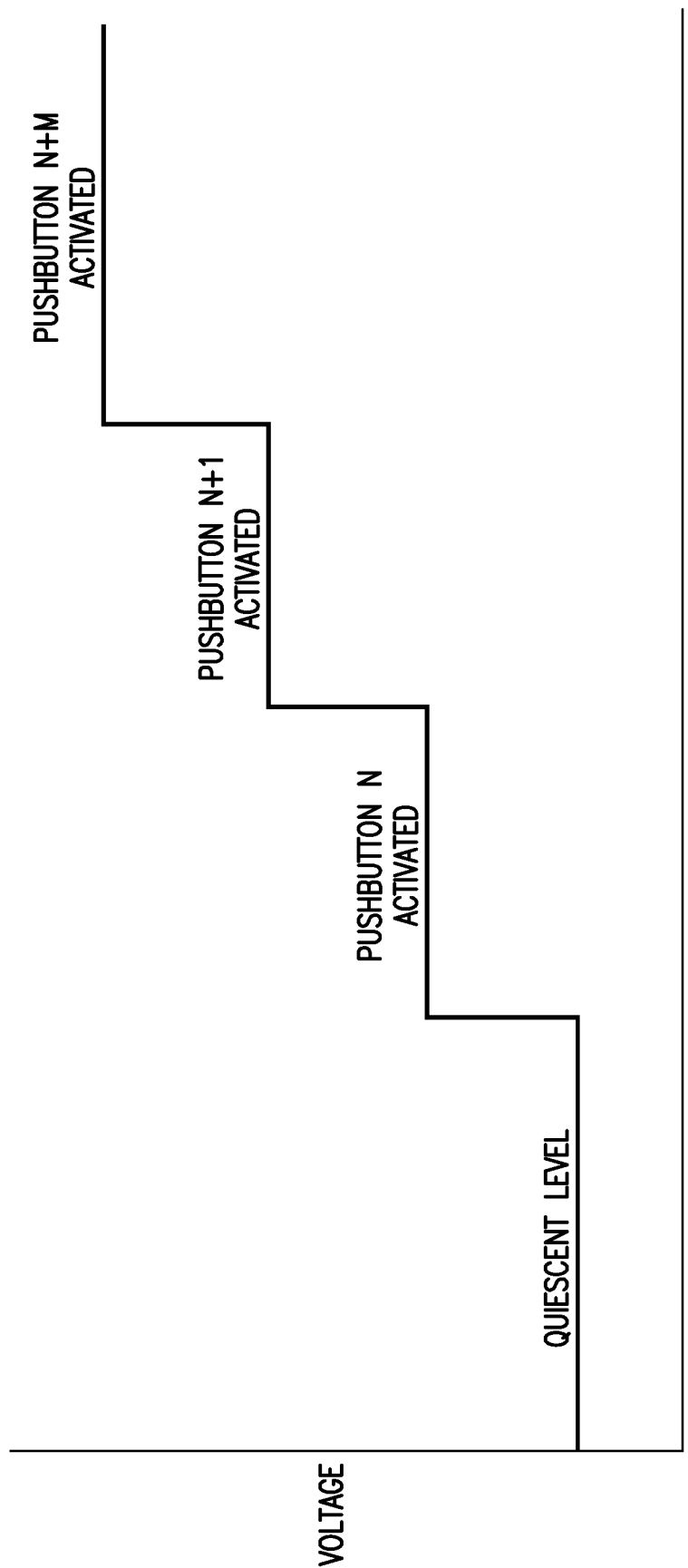
FIG. 10 is an illustration of an activation sense output for multiple pushbuttons in accordance with an embodiment of the present disclosure.

Potentially any number of additional pushbuttons could be added to the electrosurgical hand piece by using other resistor and capacitor values sufficiently different that the change in impedance could be reliably recognized by a multi-button activation sensing circuit, given the constraints of the electrical noise present in an electrosurgical environment. Electrosurgical processes essentially consist of an arc discharge into the operative site and produce a wide frequency spectrum of noise which varies considerably both in time and in amplitude. An example of multi-button sensing is illustrated in FIG. 10.

In one embodiment, the electrosurgical generator coupled to the electrosurgical apparatus 200 includes an activation sense circuit configured to sense impedances values along the conductors of cable 210 to determine which button or switch has been activated. The output of the activation sense circuit is sent to an analog to digital converter (ADC) which converts the different voltage levels into an equivalent digital representation. This digital value is compared by a controller, e.g., a microcontroller, in the electrosurgical generator to a previously stored value, and the appropriate action is taken. Alternately, the output of the activation sense circuit may be sent to an array of analog comparators, each comparing the activation sense output with a preset analog value. Again, when a particular activation sense output voltage level is recognized, the appropriate action is taken, e.g., increase a power level, decrease a power level, activate a cut mode, activate a coagulation mode, etc.

An exemplary multi-button activation sense circuit 300 will now be described in relation to FIG. 11. An oscillator generator 302 is provided which produces a sine wave, although other waveforms could be used, operates drive transistors Q2 and Q3. The configuration of these transistors operates as a voltage source, although alternately, a current source configuration could be used. The frequency of the oscillator generator 302 is chosen so that it is easily distinguished from the operating frequency of the electrosurgical generator as well as any electrosurgical power modulation frequencies. The output of the drive transistors Q2, Q3 operates the series resonant circuit consisting of components capacitor C17, inductor L3, the secondary of transformer T2, inductor L4, resistor R18 and resistor R2. This resonant circuit, and particularly the values of inductors L3 and L4, prevents the electrosurgical power signal from being picked up by the activation sense circuit.

Due to the wide spectrum of noise frequencies produced by the electrosurgical arc, several noise filtering capacitors are used, including C23 and C27, C25, C10 and C18, and C15 and C21. These last two filter capacitors C15 and C21 also prevent any stray signals produced by this circuit from entering the electrosurgical system power supply, as well as preventing stray signals which may be present in the system power supply from affecting this activation circuit.

The current sensed by isolation barrier transformer T2 is sent to a voltage divider consisting of R2 and R18, whose output is subsequently rectified and filtered and sent to the ADC (not shown). This sensed current is also sent to the cut or coagulation activation circuit consisting of R13, D2 and the associated comparator 304.

Figure 11:
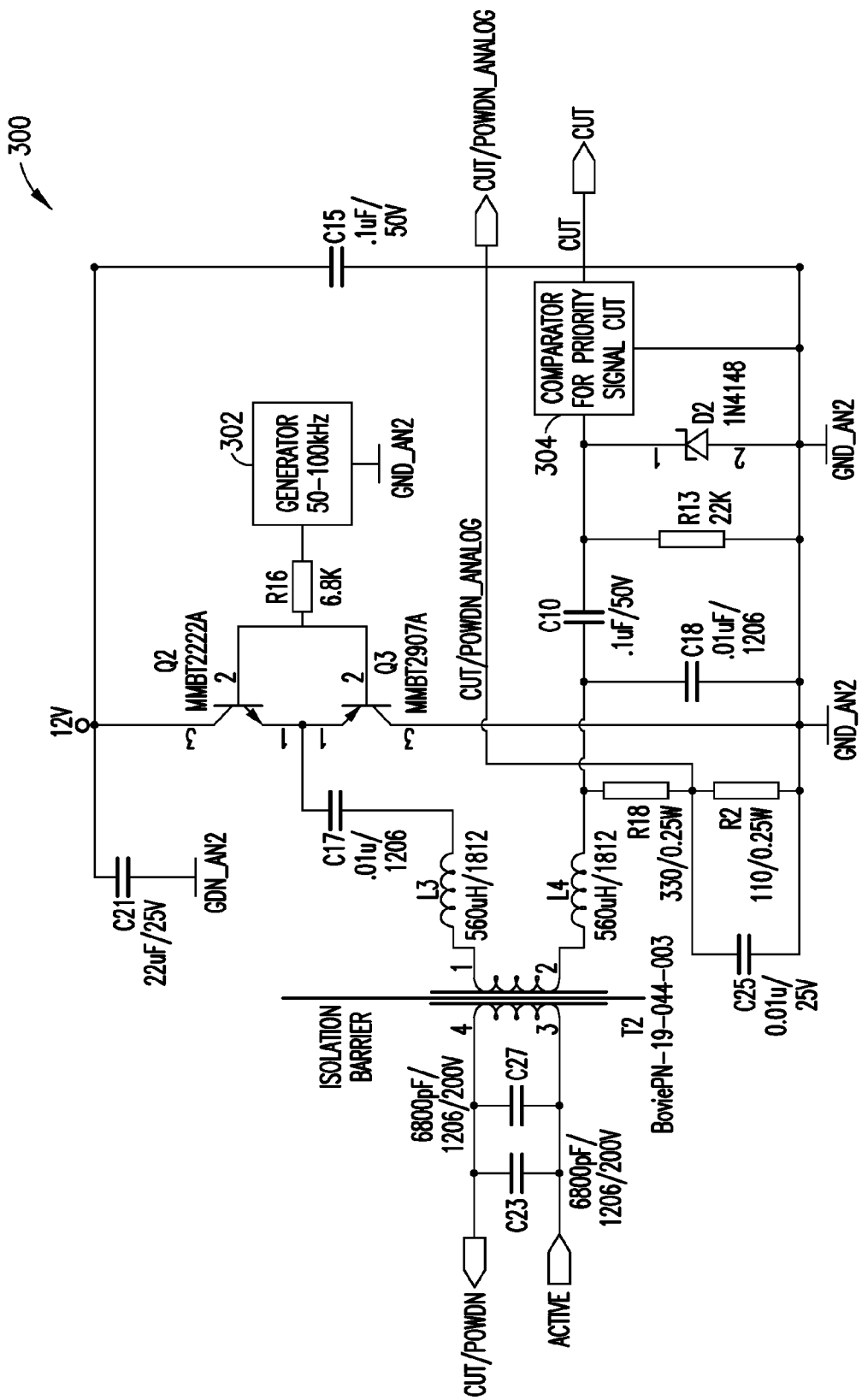
FIG. 11 is a multi-button activation sensing circuit in accordance with an embodiment of the present disclosure.

The circuit shown in FIG. 11 may be used to sense the activation, for example, of the cut pushbutton or the power-down pushbutton. A duplicate circuit would be used then to sense the coagulation or power-up pushbutton, as shown in FIGS. 12A-12C.

Figure 12B:
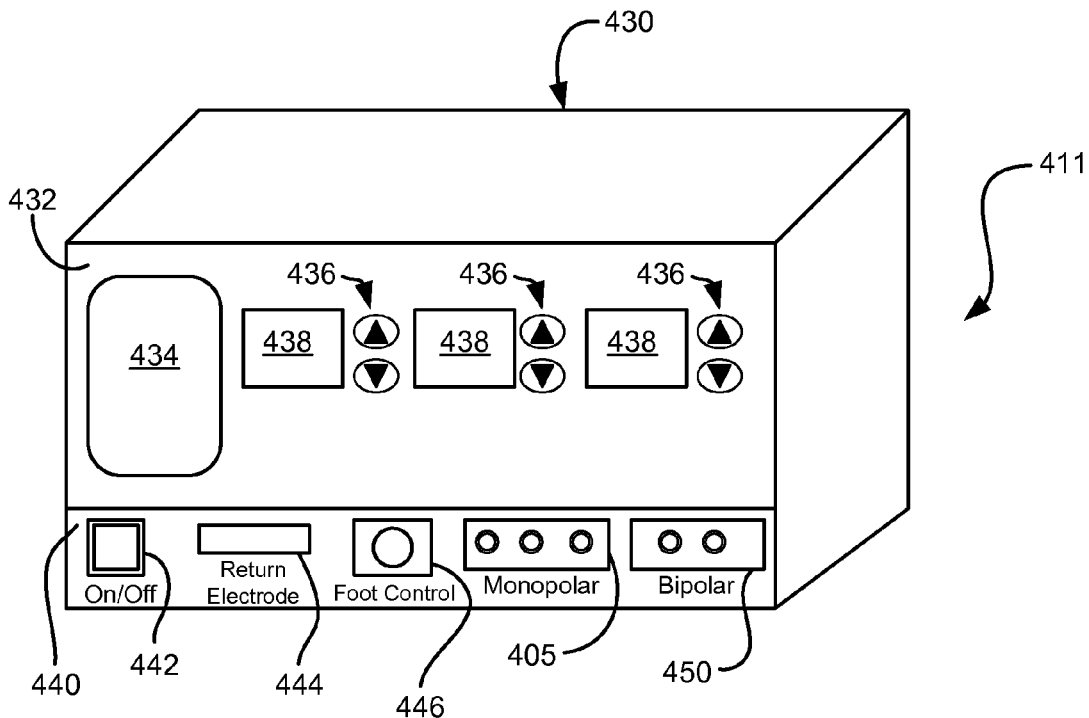
Figure 12C:
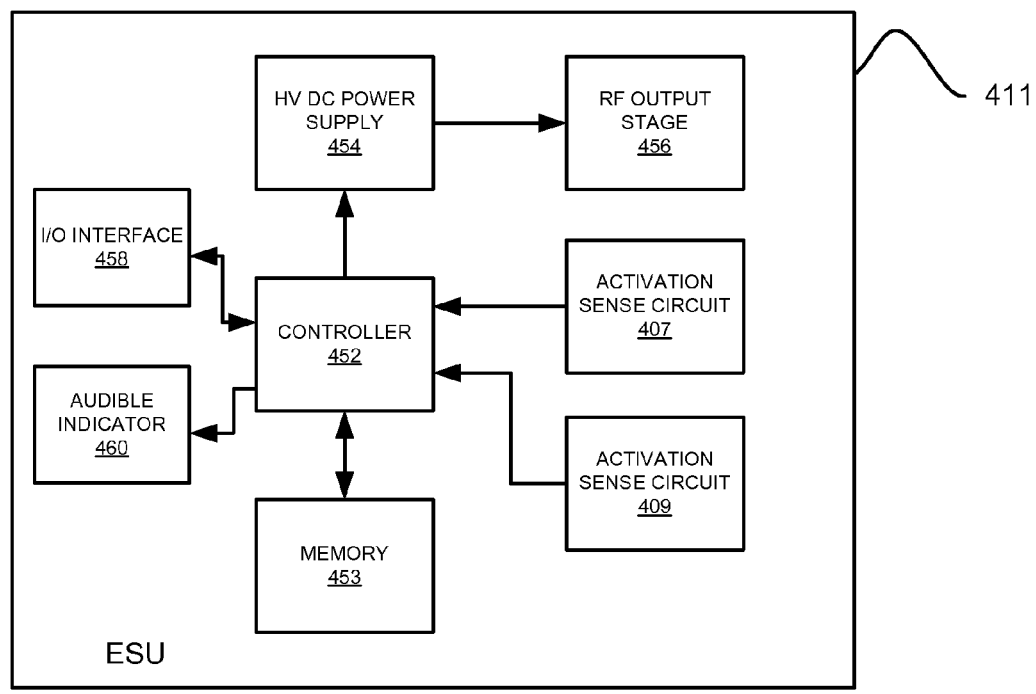

Referring to FIGS. 12A-12C, an electrosurgical system 400 is illustrated including an electrosurgical pencil 401 coupled to an electrosurgical generator 411 via a cable 403. The electrosurgical pencil 401 includes four buttons or switches, i.e., button 414 for CUT, button 416 for COAG, button 424 for power down and button 426 for power up. The cable 403 includes a connector 412, e.g., a three pin connector, for coupling the pencil 401 to the electrosurgical generator 411 via an appropriate port or receptacle 405.

Referring to FIGS. 12B and 12C, an exemplary electrosurgical generator 411 in accordance with the present disclosure is illustrated. The electrosurgical generator 411 includes a housing 430 having a front panel face 432 which includes an input section 434, e.g. a touchscreen, for entering commands and data into the generator and various level controls 436 with corresponding indicators 438. The electrosurgical generator 411 further includes a receptacle section 440 which includes a On/Off switch 442, a return electrode receptacle 444, a monopolar footswitching receptacle 446, monopolar handswitching receptacle 405 and a bipolar handswitching receptacle 450. Internally, the electrosurgical generator 411 includes a controller 452 that controls a HV DC power supply 454 (which receives power from an external source) to supply electrosurgical energy being output from an RF output stage 456 via at least one conductor 403 to the handpiece 401 in FIG. 12A. A memory 453 is coupled to the controller 452 and is configured to store various control parameters such as, but not limited to, power curves for associated handpieces, predefined power limit controls, power level increment/decrement units, predetermined impedance values associated to a switch or function, etc. The electrosurgical generator 411 will indicate various operating conditions to an operator via an I/O interface 458 such as the input section 434, level controls 436 and indicators 438. The electrosurgical generator 411 may further include an audible indicator 460 to alert an operator to various conditions.

In one embodiment, the electrosurgical generator 411 includes two activation sense circuits, i.e., circuit 407 to sense the coagulation or power-up pushbutton and circuit 409 to sense the cut or power-down pushbutton. Each activation sense circuit generates two activation signals which are transmitted to a controller 452, e.g., a processor, in the electrosurgical generator 411 to affect a corresponding action. For example, circuit 407 is configured to generate a COAG activation signal 413 and a power up activation signal 415 and circuit 409 is configured to generate a CUT activation signal 417 and a power down activation signal 419. The operation of circuits 407 and 409 are similar to that described in relation to the circuit 300 shown in FIG. 11.

It is to be appreciated that by employing the activation sense circuits of the present disclosure four buttons or switches may be implemented by the electrosurgical pencil 401 while a conventional three-pin connector 412 is employed. It is further to be appreciated that the activation sense circuits may be disposed in the electrosurgical generator 411 or may be configured as a separate module or device to be utilized with an electrosurgical generator.

Just as the electrosurgical generator produces both visual and audible feedback cues when the cut or coagulation pushbuttons are activated, the power-up and power-down pushbuttons would also produce their own feedback cues which are easily distinguished from those associated with the cut and coagulation activation. For example, the feedback cues may be in the form of a visual indictor, e.g., indicators 438, on the front panel 432 of the electrosurgical generator or in the form of a audible indictor, e.g., audible indicator 460, producing a sound from the electrosurgical generator.

The electrosurgical generator could also have the capability to have pre-set limits for remote power-up or power-down activation so that the output power of the electrosurgical generator is not inadvertently raised to dangerously high levels, or reduced to levels that are ineffective.

Figure 13:
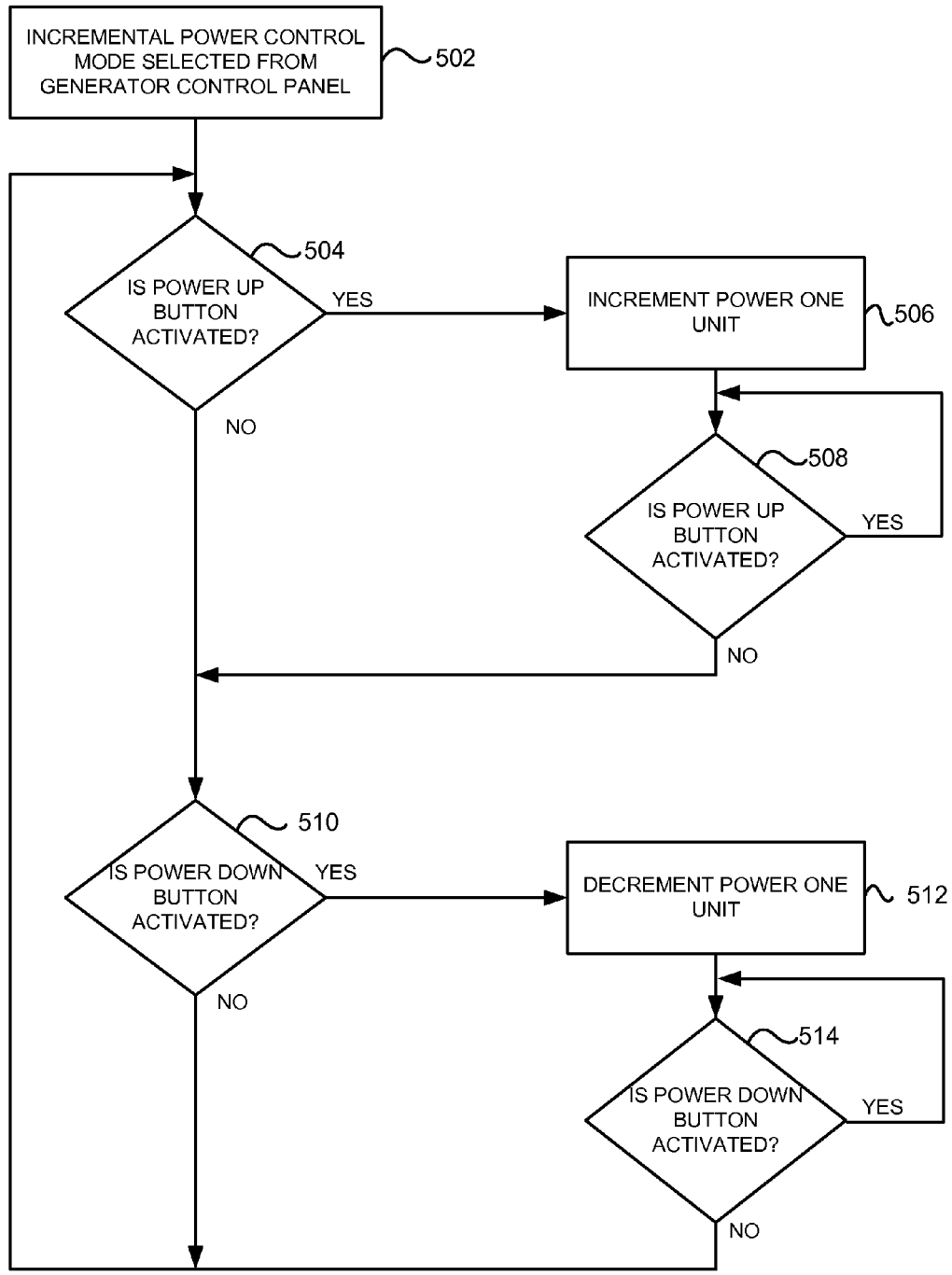
FIG. 13 is a flow chart illustrating an incremental power control mode in accordance with an embodiment of the present disclosure.

Different methods of remote power increase or decrease, via the buttons of the handpiece, may be employed. For example, a single depression of the power-up pushbutton may increase the electrosurgical generator's power output by a pre-set fixed amount. A subsequent depression of this pushbutton would increase the power output again by the same amount. An exemplary incremental power control mode is illustrated in FIG. 13. Initially, in step 502, the incremental power control mode is selected from the generator control panel, e.g., input section 434. Next, the controller determines if the power up button is activated in step 504. If the power up button is activated, the controller 452 increments a power level one unit, step 506. At step 508, the controller 452 determines if the power up button is still activated, and if so, no further action is taken. The power up button must first be released, and if pressed again, another increment of one unit of the power level is taken. In this way, the power level will be incremented by as many units as the power up button is repeatedly pressed. For example, if the power up button is pressed three times, the power level will be increased by three units.

If the controller 452 determines the power up button is not activated in steps 504 and 508, the controller 452 performs similar steps for decrementing the power level in steps 510-514. It is to be appreciated that the size of the increment/decrement unit is to be entered or adjusted at the control panel of the electrosurgical generator, for example, via level controls 436. In another embodiment, the size of the increment/decrement unit may be programmed into the generator to be fixed. In another embodiment, the generator may be programmed with a high and/or low power limit level, where when the limit level is reached, further button activations will have no effect. In a further embodiment, the generator includes an audible indicator 460 that is activated each time the power level is incremented or decremented.

Figure 14:
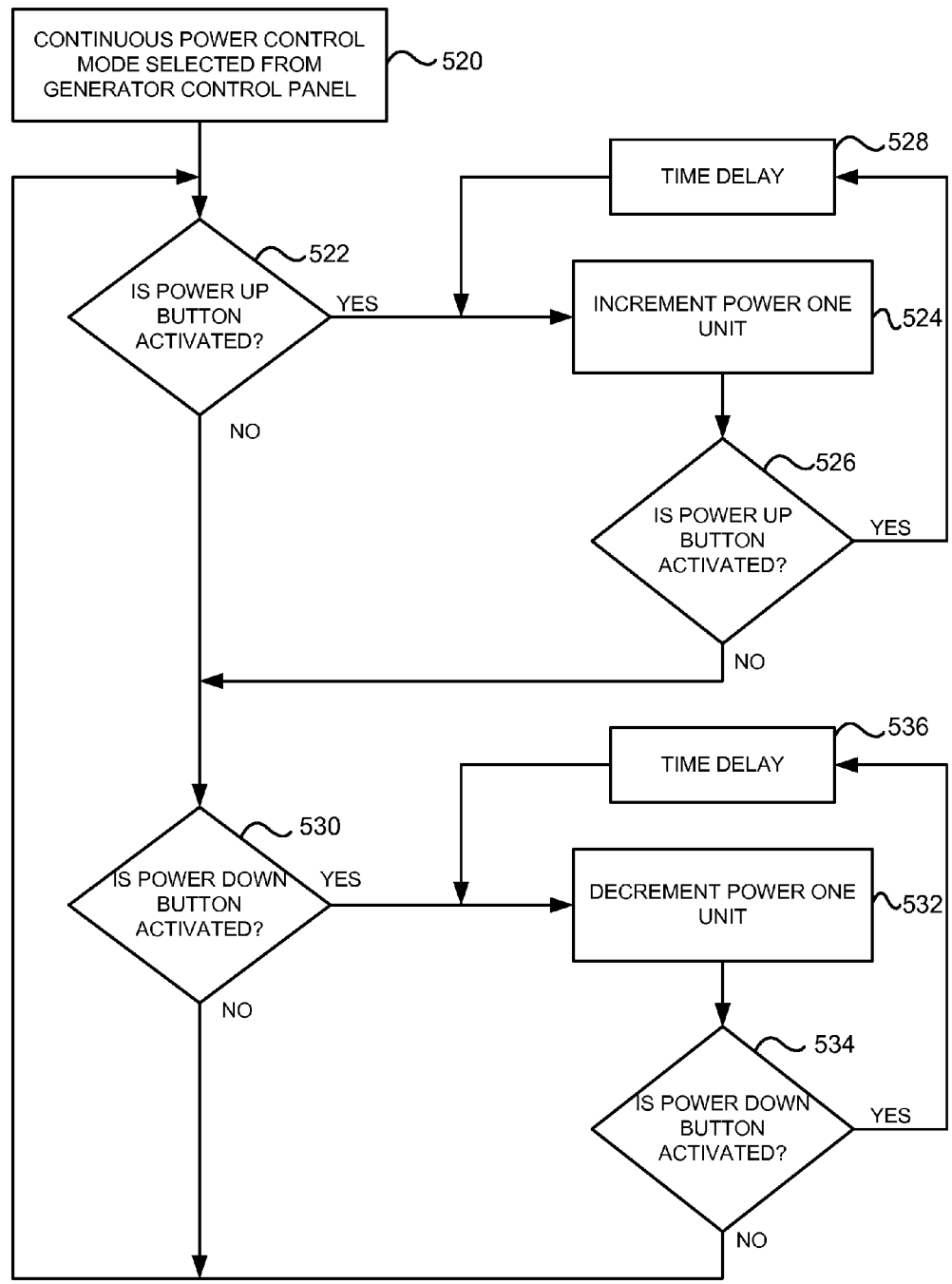
FIG. 14 is a flow chart illustrating a continuous power control mode in accordance with an embodiment of the present disclosure.

Alternately, a single depression of this pushbutton would again increase the output power by a fixed amount, but continuing to hold it down would continue to advance the power setting, with the appropriate visual and audible feedback cues being issued. An exemplary continuous power control mode is illustrated in FIG. 14. Initially, in step 520, the continuous power control mode is selected from the generator control panel, e.g., input section 434. Next, the controller 452 determines if the power up button is activated in step 522. If the power up button is activated, the controller 452 increments a power level one unit, step 524. At step 526, the controller 452 determines if the power up button is still activated, and if so, the controller 452 initiates a time delay, step 528, before incrementing the power level one more unit. The duration of the time delay determines how fast the power level is incremented. A short time delay will cause the power level to be incremented rapidly as long as the power up button remains pushed. A longer delay will cause the power level to be incremented more slowly. The duration of the delay can either be set by the generator front panel, e.g., via input section 434 or level controls 436, or pre-set to a fixed value by the manufacturer.

If the controller 452 determines the power up button is not activated in steps 522 and 526, the controller 452 performs similar steps for decrementing the power level in steps 530-536.

It is to be appreciated that once the power level is set, for example, by the methods described in relation to FIGS. 13 and 14, the cut or coagulation mode can be implemented by pressing the appropriate button. As described above, once the CUT or COAG button is activated or pressed, the power up and/or power down buttons will have no effect.

Additional pushbuttons and functionality could be added to the electrosurgical hand piece using both the cut and coagulation lines, within the limits of user convenience, complexity, and safety. For example, in plasma beam-type electrosurgical devices, additional pushbuttons or switches could be used to adjust the gas flow rate as well as electrical beam power levels from the hand piece.

While the oscillator generator 302 in FIG. 11 operates at one fixed frequency, an alternate embodiment may include a variable frequency oscillator generator. Such a variable frequency may be swept periodically through a given range of frequencies, or step through a given set of specific frequencies periodically. When additional switches (e.g., switches 225 or 227 shown in FIG. 9) are activated, a resonant circuit or device is switched in and sensed by activation sensing circuit 300 in FIG. 11, except that now the change in impedance is correlated with the specific frequency.

For example, if the resonant circuits or devices attached to switches 225 and 227 in FIG. 9 are designed to have resonant frequencies of 30 kHz and 35 kHz respectively, then when oscillator generator 302 in FIG. 11 either sweeps through or steps through those frequencies and no change in impedance is detected by circuit 300 in FIG. 11, then neither switch 225 nor 227 was activated. If, however, a change in impedance is detected when oscillator generator 302 is at 30 kHz, then the circuit 300 will determine that switch 225 was activated. Similarly, if the oscillator generator 302 is at 35 kHz and an impedance change is detected, then the circuit 300 will determine that switch 227 was activated.

Potentially any number of additional pushbuttons could be added to the electrosurgical hand piece by using other resonant circuit or device values sufficiently different that the change in impedance could be reliably recognized by a multibutton activation sensing circuit, given the constraints of the electrical noise present in an electrosurgical environment. Electrosurgical processes essentially consist of an arc discharge into the operative site and produce a wide frequency spectrum of noise which varies considerably both in time and in amplitude.

The resonant circuit can consist of either series or parallel combinations of a resistor, an inductor, and a capacitor, or it can be a resonant device such as a crystal, ceramic resonator, or similar electromechanical resonating component. The resonant frequencies are selected such that the resonant frequencies are easily distinguished from the electrosurgical power frequency and/or any power modulation frequencies that may be used.

It is to be appreciated that the various features shown and described are interchangeable, that is, a feature shown in one embodiment may be incorporated into another embodiment.

It will be appreciated by those skilled in the art that the block diagrams presented herein represent conceptual views of illustrative circuitry embodying the principles of the disclosure. Similarly, it will be appreciated that any flow charts, flow diagrams, state transition diagrams, pseudo-code, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor ("DSP") hardware, read only memory ("ROM") for storing software, random access memory ("RAM"), and nonvolatile storage.

Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. An electrosurgical apparatus comprising:
    a housing having a proximal end and a distal end, the distal end configured to support an electrode;
    at least four switches disposed on a surface of the housing configured to be selectively activated by a user; and
    three wires connected between the housing and a connector, the connector configured to be operatively coupled to an electrosurgical generator, a first wire being coupled to the electrode and configured to receive electrosurgical energy from the electrosurgical generator, a second wire being coupled to a first switch of the at least four switches and configured to generate a first activation signal and a third wire being coupled to a second switch of the at least four switches and configured to generate a second activation signal,
    wherein a third and fourth switch of the at least four switches are coupled to the first wire and the second or third wire via a respective reactive switching element configured to generate third and fourth activation signals.

2. The electrosurgical apparatus as in claim 1, wherein the at least four switches are configured as pushbuttons.

3. The electrosurgical apparatus as in claim 1, wherein each of the respective reactive switching elements is selected to generate a different impedance value.

4. The electrosurgical apparatus as in claim 3, wherein each of the first and second activation signals is a short circuit signal.

5. The electrosurgical apparatus as in claim 3, wherein each of the respective reactive switching elements is a parallel combination of a resistor and a capacitor.

6. The electrosurgical apparatus as in claim 3, wherein each of the respective reactive switching elements is a series combination of a resistor and an inductor.

7. The electrosurgical apparatus as in claim 3, wherein each of the respective reactive switching elements is a series combination of a resistor and a capacitor.

8. The electrosurgical apparatus as in claim 3, wherein each of the respective reactive switching elements is a parallel combination of a resistor and an inductor.

9. The electrosurgical apparatus as in claim 3, wherein each of the respective reactive switching elements is a capacitor.

10. The electrosurgical apparatus as in claim 3, wherein each of the respective reactive switching elements is an inductor.

11. The electrosurgical apparatus as in claim 1, wherein the connector includes a three pin connector.

12. The electrosurgical apparatus as in claim 1, wherein at least two switches of the at least four switches are coupled to a single rocker button.

13. An electrosurgical apparatus comprising:
    an electrosurgical generator coupled to an electrical power supply configured to generate electrosurgical energy;
    a handpiece including:
        a housing having a proximal end and a distal end, the distal end configured to support an electrode;
        at least four switches disposed on a surface of the housing configured to be selectively activated by a user; and
        three wires connected between the housing and a connector, the connector configured to be operatively coupled to the electrosurgical generator, a first wire being coupled to the electrode and configured to receive electrosurgical energy from the electrosurgical generator, a second wire being coupled to a first switch of the at least four switches and configured to generate a first activation signal and a third wire being coupled to a second switch of the at least four switches and configured to generate a second activation signal, wherein a third and fourth switch of the at least four switches are coupled to the first wire and the second or third wire via a respective reactive switching element configured to generate third and fourth activation signals; and at least one activation sense circuit configured to distinguish between the first, second, third and fourth activation signals and to execute a corresponding action.

14. The electrosurgical apparatus as in claim 13, wherein the at least one activation sense circuit includes an oscillator generator and at least one transistor configured to operate as a voltage or current source for the reactive switching elements.

15. The electrosurgical apparatus as in claim 14, wherein a frequency of the oscillator generator is different than an operating frequency of the electrosurgical generator.

16. The electrosurgical apparatus as in claim 13, wherein each of the respective reactive switching elements is selected to generate a different impedance value.

17. The electrosurgical apparatus as in claim 16, wherein each of the first and second activation signals is a short circuit signal.

18. The electrosurgical apparatus as in claim 17, wherein the at least one activation sense circuit includes a comparator to compare each of the third and fourth activation signals to a predetermined value.

19. The electrosurgical apparatus as in claim 17, wherein the at least one activation sense circuit converts the third and fourth activation signals into a respective pulse width modulation (PWM) signal.

20. An electrosurgical apparatus comprising:
an electrosurgical generator coupled to an electrical power supply configured to generate electrosurgical energy;
a handpiece including:
  a housing having a proximal end and a distal end, the distal end configured to support an electrode;
  at least four switches disposed on a surface of the housing configured to be selectively activated by a user; and
  three wires connected between the housing and a connector, the connector configured to be operatively coupled to the electrosurgical generator, a first wire being coupled to the electrode and configured to receive electrosurgical energy from the electrosurgical generator, a second wire being coupled to a first switch of the at least four switches and configured to generate a first activation signal and a third wire being coupled to a second switch of the at least four switches and configured to generate a second activation signal, wherein a third and fourth switch of the at least four switches are coupled to the first wire and the second or third wire via a respective resonant circuit configured to generate third and fourth activation signals; and
at least one activation sense circuit configured to distinguish between the first, second, third and fourth activation signals and to execute a corresponding action.

21. The electrosurgical apparatus as in claim 20, wherein the at least one activation sense circuit includes an oscillator generator and at least one transistor configured to operate as a voltage or current source for the resonant circuits.

22. The electrosurgical apparatus as in claim 21, wherein each respective resonant circuit is configured for a different frequency.

23. The electrosurgical apparatus as in claim 22, wherein the oscillator generator is a variable frequency oscillator generator configured to sweep through a predetermined range of frequencies, wherein the predetermined range of frequencies include the frequencies of the respective resonant circuits.

\* \* \* \* \*